United States Patent [19]

Mattila et al.

[11] Patent Number: 4,885,461
[45] Date of Patent: Dec. 5, 1989

[54] OBJECT IDENTIFYING DEVICE

[75] Inventors: Timo Mattila; Juha Elf, both of Kausala, Finland

[73] Assignee: Halton Oy, Finland

[21] Appl. No.: 162,872

[22] Filed: Mar. 2, 1988

[30] Foreign Application Priority Data

Mar. 2, 1987 [FI] Finland .................................. 870904

[51] Int. Cl.$^4$ ............................................. G01N 9/04
[52] U.S. Cl. ................................. 250/223 B; 356/240
[58] Field of Search .................... 250/223 B; 356/240; 209/524, 525, 529, 576, 577

[56] References Cited

U.S. PATENT DOCUMENTS

| | | | |
|---|---|---|---|
| 3,563,379 | 2/1971 | Stapf | 356/240 |
| 3,955,179 | 5/1976 | Planke | 356/240 |
| 4,367,405 | 1/1983 | Ford | 356/240 |
| 4,620,090 | 10/1986 | Ducloux | 250/223 B |

FOREIGN PATENT DOCUMENTS

| | | | |
|---|---|---|---|
| 2837112 | 1/1979 | Fed. Rep. of Germany ... | 250/223 B |
| 52-4950 | 4/1977 | Japan .................................. | 250/223 B |

Primary Examiner—Edward P. Westin
Assistant Examiner—Khaled Shami
Attorney, Agent, or Firm—Steinberg & Raskin

[57] ABSTRACT

Object identifying device, e.g. a bottle receiving device, comprising a transport apparatus for transporting the objects such as bottles, an identifying device with a data processing unit for identifying and accepting bottles having certain given shapes, and a recording device for recording accepted bottles. The identifying device comprises a principally stationary illuminating device for illuminating the bottles, a detector for examining the bottles, and a conveyor for moving the bottles past the detector. A mirror system is interposed between the illuminating device and the detector, with which the optical length of the entire system can be increased without increasing the structural dimensions thereof.

16 Claims, 2 Drawing Sheets

OBJECT IDENTIFYING DEVICE

BACKGROUND OF THE INVENTION

The present invention concerns bottle receiving means comprising transport means for transporting bottles, identifying means with a data processing unit for identifying and accepting bottles having given shapes, and recording means for recording the accepted bottles. The identifying means comprise a chiefly or mainly stationary illuminating means for illuminating the bottle, a detector for examining the bottle, and a conveyor for moving the bottle past the detector.

Bottle receiving means are known in the prior art, based on use of a laser beam, in which the shape of the bottle is examined with the aid of a laser beam reflected on the bottle with the aid of a rotating mirror. The information on the shape of a bottle is obtained with the aid of a detector consisting of optic fibers. Accepted bottles are identified in a processing unit, to which the information on the respective bottle under examination is conducted in the form of electrical signals in order to compare the shape information of the bottle under examination with equivalent data of acceptable bottle shapes provided in a file. Information on accepted bottles is conducted to a recording unit which records the number of accepted bottles and, for instance, their type and/or possibly the amount of money to be refunded for the bottles on a voucher which may be debited by a checkout attendant.

Bottle receiving means are particularly well usable in the bottle returning departments of major foodstuff stores and department stores, and stores for selling beer.

The bottle receiving means of the prior art is susceptible to malfunctions, inasmuch as the laser is a sensitive component and the rotating mirror requires extremely exact aligning. This makes the manufacturing of the bottle receiving means rather difficult, and results in high cost of the same. Furthermore, natural wear of the means causes need for servicing, since the various parts of the means require special precision for faultless operation.

Bottle receiving means have been disclosed in Finnish Patent No. 71892, comprising transport apparatus for transporting bottles, identifying means for identifying and accepting bottles having given shapes, and recording means for recording accepted bottles. The identifying means comprise a principally or mainly stationary illuminating means for illuminating the bottle, a detector for examining the bottle, and a conveyor for moving the bottle past the detector. The detector contains a lineal camera arranged to examine the bottle momentarily at lineal locations, while the bottle moves past in front of the detector as moved by the conveyor, so that the lineal examined locations provide information at least on the shape of the neck of the bottle and upper part thereof. The detector is mainly constituted by photo-diodes disposed in a row. The conveyor is disposed to transport the bottle between the illuminating means and the detector, so that the detector will examine the bottle from behind, referring to the illuminating means, and will supply information on the shape of the bottle on the basis of the shadow thrown by the bottle.

This particular solution in the prior art is based on examining the bottle that has been turned in, at discrete moments and at lineal locations, while the bottle is moving past the detector. As the bottle moves, the lineal examining location will thereby sweep over the entire bottle and a line image of the bottle will be obtained over the entire body. To perform this examination, a lineal camera may be advantageously used, which is simple in construction and advantageous regarding cost. The line image, e.g. a signal sequence of electrical pulses delivered by the lineal camera, is extremely appropriate for processing the image and shape of a bottle with a view to identifying accepted bottle shapes and recording accepted bottles.

If desired, for instance in conjunction with the lineal camera, the bottle may be illuminated with any illuminating means or lamp known in the art. If desired, it is possible to use, e.g. photodiodes arranged in a row instead of a lineal camera, in which case the bottle is appropriately illuminated from the opposite side, e.g. with the aid of light-emitting diodes, for instance with infra-red LED's arranged in a row. In that case, the examination may be timed to take place at given time intervals as the bottle is moving past between the illuminating means and the light diodes, in order to obtain a line image of the respective bottle under examination.

The detector and receiver means are placed directly opposite one another in the design disclosed in Finnish Patent No. 71892. The detector has the design of a lineal semi-conductor camera comprising a camera element and optics. Since the camera and the illuminating means are opposed, the mechanical dimensions of the means impose certain requirements on the optics of the camera, i.e. wide-angle optics are required. This has the consequence that in this solution of the prior art, a powerful parallax error is incurred. In other words, even minor displacement of the bottle on the line connecting the detector and the illuminating means, causes a considerable error in the result of measurement attained from a bottle on the conveyor.

In the solution disclosed in Finnish Patent No. 71892, the position of the bottle on the conveyor must be exactly correct, in which case the height is $h_1$. If the position of the bottle is incorrect, then the height of the bottle will then be $h_2$. The positional error $\Delta s$ of the bottle on the conveyor causes error in height $\Delta h = h_2 - h_1$. On the strength of the foregoing, the accuracy requirements of this measuring system of the prior art are exceedingly high.

SUMMARY OF THE INVENTION

Accordingly, it is an object of the present invention to achieve improvement over bottle receiving means disclosed in the prior art, notably in Finnish Patent No. 71892.

It is also an object of the present invention to provide bottle receiving means in which accuracy of measurement can be substantially improved without need to position a camera or detector further away which would increase the mechanical dimensions of the bottle receiving means.

It is an additional object of the present invention to increase optical length of a device for identifying objects such as a bottle receiving device, without increasing the overall structural dimensions of such a device.

These and other objects are attained by the present invention which is directed to a device for identifying objects, comprising illumination means for illuminating objects, a detector for examining the illuminated objects and means for increasing optical length of the device without increasing structure dimensions of the same, which comprise a mirror system situated between the illumination means and the detector. Means for conveying the objects to be identified past the detector, may also be provided, while transport means for transporting the objects to and from the conveyor means may be provided too, along with a data processing unit coupled to said detector, for identifying and accepting objects having certain given shapes, and recording means coupled to said data processing unit for recording accepted objects. The objects themselves, may be bottles. Additionally the illuminating means may be chiefly or principally stationary.

The aims and objects of the present invention are achieved with bottle receiving means which is principally characterized by a mirror system having been inserted between the illuminating means and the detector, by which the optical length of the system can be altered, i.e. increased without increasing the overall structural dimensions of the bottle receiving means.

Due to the particular solution presented by the present invention, even major positional errors, Δs of the bottles on the conveyor, cause no worth-while error in height Δh, which approaches zero with increasing focal length.

The essence of the concepts of the present invention, is attained by the mirror system by means of which the optical length of the measuring system can be increased. Theoretically, the optical length may approach infinity, if infinitely high manufacturing accuracy is reached. Naturally in practice, such manufacturing accuracy is, in actual fact, not even necessary.

The mirror system of the present invention may have one, two, three, or if required, even more mirrors. The light traveling from the illuminating means to the detector is then reflected through one mirror to the detector, or through two mirrors to the detector, or through three mirrors to the detector in which case the first mirror is an auxiliary mirror and the second and third mirrors are principal mirrors, or through four mirrors to the detector in which case the first and fourth mirrors are auxiliary mirrors and the second and third mirrors are principal mirrors. In the embodiments with three or four mirrors, or in an embodiment in which an even greater number of mirrors is used, the mirrors are positioned in a specific manner, i.e. are situated and installed at an angle of reflection. It is essential that the angles between mirrors are set to conform to the principles and laws of the theory of optics and of reflection.

BRIEF DESCRIPTION OF THE DRAWINGS

The present invention will now be described in greater detail, with reference to certain preferred embodiments thereof illustrated in the accompanying figures to which, however, the present invention is not intended to be exclusively confined. In the drawings.

DESCRIPTION OF THE PREFERRED EMBODIMENTS

Figure 1:
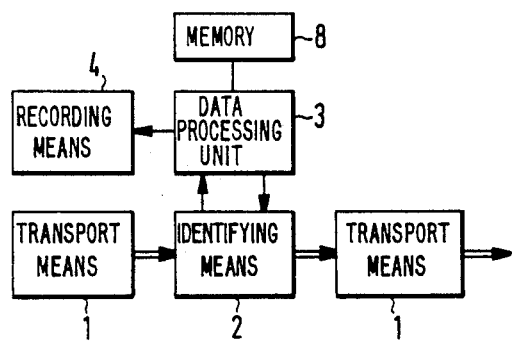
FIG. 1 is a block diagram illustrating the principles of design and operation of bottle receiving means according to the present invention.

Application of bottle receiving means conforming to an embodiment of the present invention is presented by way of example in FIG. 1. Referring to this figure, the bottle receiving means comprises transport means 1 for transporting bottles, identifying means 2 with a data processing unit 3 for identifying and accepting bottles having given shapes, and recording means 4 for recording the accepted bottles. The transport means 1 may be constituted by e.g., one or several belt conveyors, by a rotary disc conveyor, or in general any kind of conveyor suitable for transporting bottles. The conveyor may be disposed to transport bottles in a horizontal direction and/or possibly in a vertical direction. However, horizontal transport is considered most appropriate in connection with bottle receiving means according to the present invention. The transport apparatus may further comprise feeder means for feeding bottles to the transport means, and removal means for removing the bottles at the end of the transport means, e.g. onto the floor of a storage space, into a bottle hamper, etc.

The identifying means 2 advantageously comprise a data processing unit 3 with a memory unit 8 and a recording unit 4, if any. The data processing unit 3 is thus provided with a file specifying acceptable bottle shapes. In other words, the data of acceptable bottle shapes may be entered into the file for comparison of the information obtained from bottles with the equivalent information on acceptable bottle shapes. The recording means record the number of acceptable bottles, possibly the sizes thereof and/or the amount of money to be debited or refunded.

Figure 2:
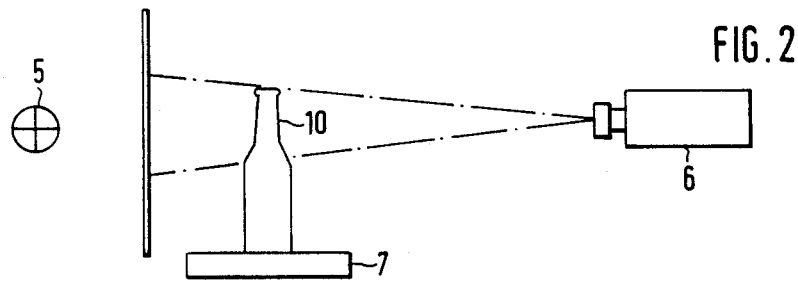
FIG. 2 is an elevational view illustrating the principles of construction of identifying means belonging to receiver means illustrated in FIG. 1.
Figure 3:
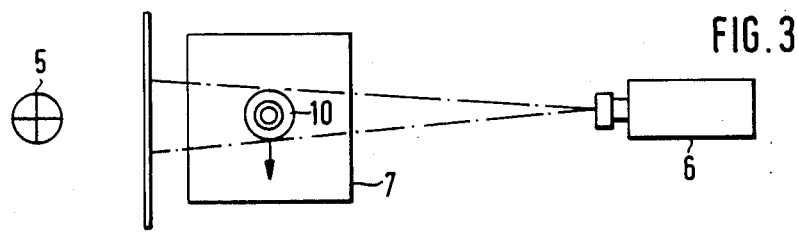
FIG. 3 is a top view of the identifying means illustrated in FIG. 2.

In FIGS. 2-3, identifying means 2 are seen in a schematic principle diagram, as comprising chiefly or mainly stationary illuminating means 5 for illuminating a bottle 10, a detector 6 for examining the bottle 10, and a conveyor 7 for moving the bottle 10 past the detector 6. The detector 6 has been disposed to examine the bottle 10 at discrete moments, at time intervals, at lineal locations, as the bottle 10 moves, as transported by the conveyor 7, past the detector 10 in such a manner that the lineal examined locations yield information at least on the shape of the bottle neck and upper part thereof. In other words, the detector 6 is disposed to register a so-called line image of the bottle 10.

Figure 4:
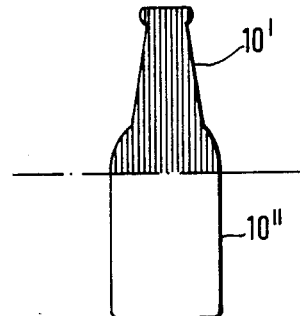
FIG. 4 illustrates formation of a line image of a bottle under examination with the identifying means illustrated in FIGS. 2 and 3.

It is thus understood that when registering this line image, the detector 6 registers, at intervals, line images of the bottle 10 as shown in FIG. 4, while the bottle 10 is moving past the detector 10 on the conveyor 7. Such line images may be taken at desired time intervals. In other words, the line spacing of the image can be regulated as desired according to the desired accuracy of information. The detector 6 converts the line image received into electric pulses, to be conducted to a data processing unit 3 as shown in FIG. 1, in a manner known in and of itself in the art.

It is not absolutely necessary to register a line image of the entire bottle 10. It is usually sufficient to project the image of the upper part 10' of the bottle 10 as shown in FIG. 4, since the specific characteristics of different bottle types and models are usually most apparent in the upper part of the bottle 10. The lower part 10' of the bottle 10 is then appropriately excluded from the image process.

In FIGS. 2 and 3, a conventional lineal camera has been used for the detector 6, this camera being arranged to produce an image of the bottle 10 moving past in front of the camera 10 in a lateral direction, at right angles against the alignment of the camera objective, in the region of the upper part of the bottle neck in the form of vertical line images at 1 mm spacing. The identifying means have been programmed to measure the height of the bottle 10. If desired, the detector 6 may be arranged to produce horizontal images of the bottle 10, in which case the conveyor 7 is appropriately disposed to transport the bottle 10 in a vertical direction, for viewing the bottle at desired height.

By using a lineal camera for the detector 6, certain advantages are attained compared, for instance, to identifying means based on the laser. In the first place, a lineal camera is substantially less expensive than a laser. The lineal camera usually requires far less maintenance than any laser apparatus. The lineal camera is reliable in operation and construction, tolerating vibration and other external stresses. The lineal camera may, for instance, be a so-called CCD (Charge Coupled Diode) camera, or, for instance, a so-called photodiode camera (Self Scanning Array). A lineal camera may further be easily connected to a data processing unit 3, while the information delivered by the lineal camera, i.e. an electric signal sequence, is eminently suited to be used substantially as is in a data processing unit 3. Furthermore, the lineal camera 6 can be easily adjusted and timed regarding scanning rate, i.e. the image-recording interval.

Figure 5:
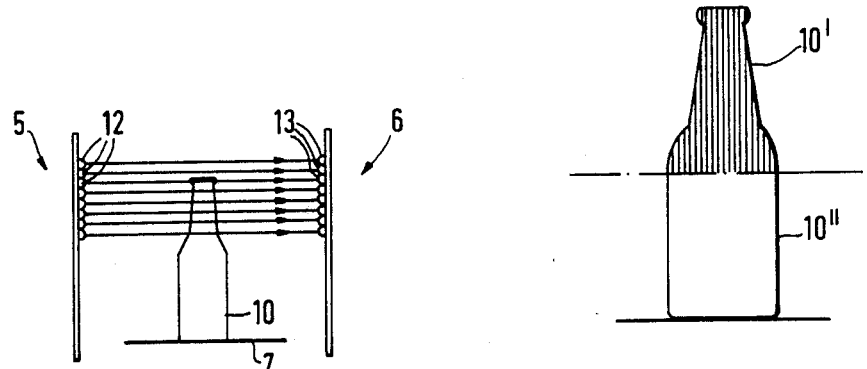
FIG. 5 is an elevational view of another embodiment of the identifying means of the present invention.

Another embodiment is illustrated in FIG. 5 in which the bottle 10 under examination is conducted to pass on a conveyor 7 through a gate constituted by a row of diodes 12 emitting IR (infrared) light and a vertical row formed by light-receiving photo-diodes 13. The IR light-emitting diodes and the corresponding light-measuring photo-diodes then constitute identifying means 2 in which the diodes 12, 13 have been arranged to measure the height of the bottle 10 at time intervals, i.e., to record vertical line images of the bottle 10. The timing of the photo-diodes 12, 13 is used to regulate the line spacing of the line image, i.e., the resolution of the image.

In the embodiments presented herein, the bottle 10 under examination has been disposed to be transported in upright position. However, if desired, the transport means 1 and/or the conveyor 7 may be arranged to move the bottle 10 relative to the detector 6 in horizontal position as well, i.e. with the mouth of the bottle 10 pointing in a horizontal direction. Furthermore, in the embodiments that have been presented herein, the detector 6, i.e. the lineal camera or the row of photo-diodes 13, has been disposed to be stationary. Alternatively, the lineal cameras or the photo diodes 13 may be equally disposed to scan the bottle 10 for recording an image of the bottle 10, although this last-noted feature is more complex and consequently more expensive.

Figure 6:
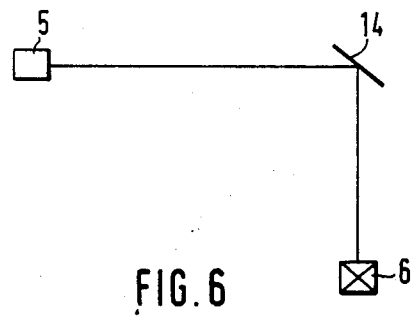
FIG. 6 illustrates a mirror system interposed between illuminating means and a detector in the bottle receiving means according to the present invention.

In the embodiment illustrated in FIG. 6, a mirror system has been interposed between the illuminating means 5 and the detector 6, this mirror system consisting of one mirror 14 in this particular embodiment.

Figure 7:
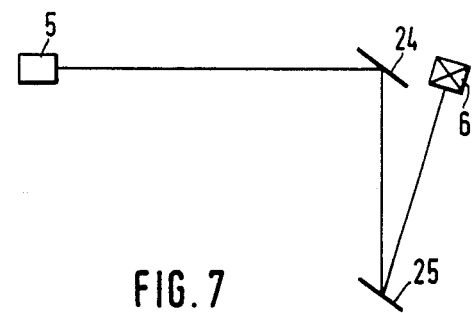
FIG. 7 illustrates another embodiment of a mirror system interposed between the illuminating means and the detector in the bottle receiving means according to the present invention.

In the embodiment illustrated in FIG. 7, a mirror system has been interposed between the illuminating means 5 and the detector 6, this mirror system consisting of a first mirror 24 and a second mirror 25 in this particular embodiment.

Figure 8:
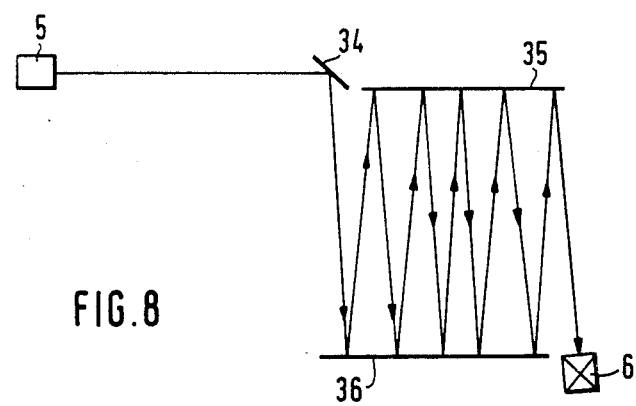
FIG. 8 illustrates a third embodiment of a mirror system interposed between the illuminating means and the detector in the bottle receiving means according to the present invention.

In the embodiment illustrated in FIG. 8, a mirror system has been interposed between the illuminating means 5 and the detector 6, this mirror system consisting, in this particular embodiment, of a first mirror 34, a second mirror 35, and a third mirror 36. The first mirror 34 is an auxiliary mirror, while the second and third mirrors 35, 36 are principal mirrors. The mirrors 34, 35 and 36 have been positioned in a specific manner so that the desired angle of reflection is obtained.

Figure 9:
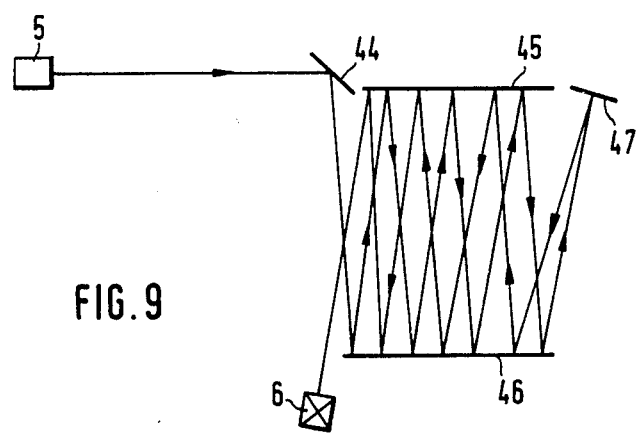
FIG. 9 illustrates a fourth embodiment of a mirror system interposed between the illuminating means and the detector in the bottle receiving means according to the present invention.

In the embodiment illustrated in FIG. 9, a mirror system has been interposed between the illuminating means 5 and the detector 6, this mirror system consisting of four mirrors 44, 45, 46, and 47 in this particular embodiment. The mirrors 44 and 47 are auxiliary mirrors, while the mirrors 45 and 46 are principal mirrors. The mirrors 44–47 have been positioned in a specific manner so that the desired angle of reflection is obtained.

The embodiments of the invention presented above are intended to illustrate the present invention in exemplary fashion only, so that the present invention may be applied without being restricted to the specific examples in any way. In other words, the preceding description of the present invention is merely exemplary, and is not intended to limit the scope thereof in any way.

What is claimed is:

1. Device for identifying objects, comprising illumination means for illuminating the objects, a detector for examining the illuminated objects, said illumination means and detector being situated opposite one another,
means for increasing optical length of said device from said illumination means to said detector without increasing structural dimensions of said device, which comprise
a mirror system situated between said illumination means and detector in a horizontal direction,
whereby reflections of the objects by said mirror system do not turn in a vertical direction.

2. Device for identifying objects, comprising illumination means for illuminating the objects, a detector for examining the illuminated objects, means for conveying the objects to be identified past said detector,
with said illumination means and detector positioned on opposite sides of said conveyor means, and
means for increasing optical length of said device from said illumination means to said detector without increasing structural dimensions of said device, which comprise
a mirror system situated between said illumination means and detector in a horizontal direction,
whereby reflections of the objects by said mirror system do not turn in a vertical direction.

3. The combination of claim 2, additionally comprising means for transporting the objects to and from said conveyor means, a data processing unit coupled to said detector, for identifying and accepting objects having certain given shapes, and recording means coupled to said data processing unit for recording accepted objects.

4. The combination of claim 3, wherein the objects are bottles.

5. The combination of claim 1, wherein said mirror system comprises at least one mirror.

6. The combination of claim 5, wherein said mirror system consists of one mirror.

7. The combination of claim 5, wherein said mirror system comprises a plurality of mirrors.

8. The combination of claim 7, wherein said mirror system consists of two mirrors.

9. Device for identifying objects, comprising
illumination means for illuminating the objects,
a detector for examining the illuminated objects, and
means for increasing optical length of said device from said illumination means to said detector means without increasing structural dimensions of said device which comprise
a mirror system situated between said illumination means and detector, whereby reflections of the objects by said mirror system do not turn in a vertical direction, and
wherein said mirror system comprises at least three mirrors. The combination of claim 7, wherein said mirror system comprises at least three mirrors.

10. The combination of claim 9, wherein said mirror system consists of three mirrors,
a first mirror nearest said illumination means being an auxiliary mirror, and
second and third mirrors being principal mirrors.

11. The combination of claim 9, wherein said mirror system comprises at least four mirrors.

12. The combination of claim 11, wherein said mirror system consists of four mirrors,
a first mirror nearest said illumination means being an auxiliary mirror,
second and third mirrors being principal mirrors, and
a fourth mirror being an auxiliary mirror.

13. The combination of claim 1, wherein said detector is a lineal camera.

14. The combination of claim 13, wherein said camera is a CCD camera or a self-scanning array photodiode camera.

15. The combination of claim 1, wherein said illuminating means are a row of IR-light-emitting diodes, and said detector is a row of light-receiving diodes.

16. The combination of claim 1, wherein said illuminating means are substantially stationary.

* * * * *